(12) United States Patent
Liu et al.

(10) Patent No.: US 7,476,752 B2
(45) Date of Patent: Jan. 13, 2009

(54) PROCESSES FOR THE PREPARATION OF 2-CYANO-3-NAPHTHALENE-1-YL-3-PHENYL-PROPIONIC ACID ALKYL OR BENZYL ESTERS

(75) Inventors: Weiguo Liu, Parsippany, NJ (US); John L. Considine, Bridgewater, NJ (US); Zhixian Ding, Fort Lee, NJ (US); John Potoski, West Nyack, NY (US)

(73) Assignee: Wyeth, Madison, NJ (US)

( * ) Notice: Subject to any disclaimer, the term of this patent is extended or adjusted under 35 U.S.C. 154(b) by 582 days.

(21) Appl. No.: 11/148,502

(22) Filed: Jun. 9, 2005

(65) Prior Publication Data

US 2005/0277783 A1  Dec. 15, 2005

Related U.S. Application Data

(60) Provisional application No. 60/579,296, filed on Jun. 14, 2004.

(51) Int. Cl.
C07C 253/30 (2006.01)
(52) U.S. Cl. .................................................. 558/357
(58) Field of Classification Search .................. 558/357
See application file for complete search history.

(56) References Cited

U.S. PATENT DOCUMENTS

| 2,878,138 | A | 3/1959 | Roderich et al. |
| 2005/0027554 | A1 | 2/2005 | Chahrouri et al. |

FOREIGN PATENT DOCUMENTS

WO  WO 2004/099150  11/2004

OTHER PUBLICATIONS

Adams et al., "Inhibition of coronary artery atherosclerosis by 17-beta estradiol in ovariectomized monkeys. Lack of an effect of added progesterone," *Arterio* (1990) 1051-1057.
Alexander et al., "Initiation of hormone replacement therapy after acute myocardial infarction is associated with more cardiac events during follow-up," *J. Am. Coll. Cardio.* (2001) 38:1-7.
Bauer et al., "Interleukin-6 in clinical medicine," *Ann Hemmatol.* (1991) 62:203-210.
Cefalu "The use of hormone replacement therapy in postmenopausal women with type 2 diabetes," *J. Women's Health & Gender-based Med.* (2001) 10:241-255.
Delyani et al., "Protection from myocardial reperfusion injury by acute administration of 17 β-estradiol," *J. Mol. Cell. Cardiol.* (1996) 28:1001-1008.
Felson et al., "The effects of estrogen on osteoarthritis," *Curr. Opinion Rheum.* (1998) 10(3):269-272.
Grodstein et al., "A prospective, observational study of postmenopausal hormone therapy and primary prevention of cardiovascular disease," *Ann. Int. Med.* (2000) 133(12):933-941.
Grodstein et al., "Postmenopausal hormone use and secondary prevention of coronary events in the nurses' health study: a prospective, observational study," *Ann. Int. Med.* (2001) 135(1):1-8.

Kurebayashi et al., "Characterization of mechanisms of interleukin-6 gene repression by estrogen receptor," *J. Steroid Biochem. Molec. Biol.* (1997) 60(1-2):11-17.
Lin et al., "Pulmonary function changes and increased Th-2 cytokine expression and nuclear factor kB activation in the lung after sensitization and allergen challenge in brown Norway rats," *Immunol. Lett.* (2000) 73:57-64.
Nathan et al., "Estradiol inhibits leukocyte adhesion and transendothelial migration in rabbits in vivo: possible mechanisms for gender differences in atherosclerosis," *Circ. Res.* (1999) 85(4):377-385.
Pelletier et al., "Osteoarthritis, an inflammatory disease: potential implication for the selection of new therapeutic targets," *Arth. & Rheum.* (2001) 44(6):1237-1247.
Reis et al., "Estrogen is associated with improved survival in aging women with congestive heart failure: analysis of the vesnarinone studies," *J. Am. Col. Cardio.* (2000) 36(2):529-533.
Roth et al., "Phytoestrogen kaempferol (3,4',5,7-tetrahydroxyflavone) protects PC12 and T47D cells from β-amyloid-induced toxicity," *J. Neurosci. Res.* (1999) 57(3):399-404.
Schonknecht et al., "Reduced cerebrospinal fluid estradiol levels are associated with increased β-amyloid levels in female patients with Alzheimer's disease," *Neurosci. Lett.* (2001) 307(2):122-124.
Sullivan et al., "Estrogen inhibits the response-to-injury in a mouse carotid artery model," *J. Clin. Invest.* (1995) 96(5):2482-2488.
Yuan et al., "Reversal of obesity- and diet-induced insulin resistance with salicylates or targeted disruption of Ikkβ," *Science* (2001) 293(5535):1673-1677.
Fadda et al., "Synthesis of some phenanthrene derivatives structurally related to certain analgesic and antipyretic drugs," *Indian Journal of Chemistry* (1990) 29B:171-173.
Gearien et al., "Catalytic hydrogenation of derivatives of α-cyano-β-(1-naphthyl) acrylic acid," *J. Am. Pharm. Assoc.* (1959) 48(1):61-63.
Chamontin et al., "Synthesis and reactivity of formyl-substituted photochronic 3,3-Dipenyl-[3H]-naphtho[2,1-b]pyrans," *Tetrahedron* (1999) 55(18):5821-5830.

(Continued)

*Primary Examiner*—Kamal A Saeed
(74) *Attorney, Agent, or Firm*—Pepper Hamilton LLP

(57) ABSTRACT

The present invention provides processes for the preparation of compounds of Formula I, which are useful in the preparation of pharmaceuticals for the treatment of inflammatory diseases. The compounds of Formula I are also useful as pharmaceuticals.

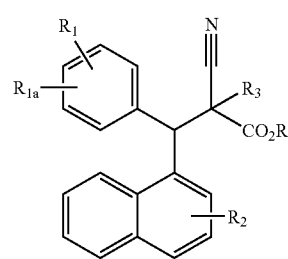

22 Claims, No Drawings

OTHER PUBLICATIONS

Harada et al., "Synthesis of human renin inhibitory peptides, angiotensinogen transition-state analogs containing a retro-inverso amide bond," *Chemical and Pharmaceutical Bulletin* (Tokyo) (1990) 38(11):3042-3047.

Helbronner "[Sur quelques derives et produits de condensation de l'aldehyde beta-oxy-alpha-napthoique,]" *Bulletin de la Societe Chimique de France* (1903) 3(29):878-882.

Hopkins et al., "Alpha-cyano-beta-arylacrylic acids," *Canadian Journal of Research. Section B., Chemical Sciences* (1945) 23:84-85.

Kisanga et al., "P(RNCH$_2$CH$_2$)$_3$N: An Efficient Promoter for the Synthesis of 3-Substituted Coumarins," *Synthetic Communications* (2002) 32(8):1135-1144.

Vistorobskii et al., "Perinaphthylenediamines. X. Acylation of proton sponge and its use for the synthesis of phenalenones," *Journal of Organic Chemistry of the USSR* (1991) 27:1353-1358.

Chen, J.J. et al. "Synthesis and Fluorescence Behavior of Some 3-Cyano-4-Substituted-6-Pyrenyl-2-Pyridone Derivatives", Dyes and Pigments, 27(3):249-259, 1995.

PROCESSES FOR THE PREPARATION OF 2-CYANO-3-NAPHTHALENE-1-YL-3-PHENYL-PROPIONIC ACID ALKYL OR BENZYL ESTERS

CROSS REFERENCE

This application claims priority benefit of U.S. Provisional Application Ser. No. 60/579,296, filed Jun. 14, 2004, which is hereby incorporated by reference in its entirety.

FIELD OF THE INVENTION

The present invention relates to processes for the preparation of substituted 3-(1-napthyl)-3-phenyl-2-cyanopropanoic acid alkyl or benzyl esters, which can be used to prepare 3-(1-naphthyl)-3-phenyl-2-cyanopropanoic acid amides useful in the treatment of inflammation.

BACKGROUND OF THE INVENTION

Ligands of the estrogen receptor (ER) have been shown to inhibit inflammatory gene expression that typically causes a reduction of cytokines, chemokines, adhesion molecules and other inflammatory enzymes. Accordingly, ER ligands can provide a means to treat inflammation such as the inflammatory component of diseases including, for example, atherosclerosis, myocardial infarction (MI), congestive heart failure (CHF), inflammatory bowel disease and arthritis. Other potential therapeutic indications for these type of molecules include type II diabetes (Cefalu, *J Womens Health & Gender-based Med.*, 2001, 10, 241; Yuan et al., *Science*, 2001, 293, 1673), osteoarthritis (Pelletier et al., *Arthr. & Rheum.*, 2001, 44:1237; Felson et al., *Curr Opinion Rheum*, 1998, 10, 269) asthma (Chin-Chi Lin et.al., *Immunol. Lett.*, 2000, 73, 57), Alzheimer's disease (Roth, A. et. al., *J. Neurosci. Res.*, 1999, 57, 399) and autoimmune diseases such as multiple sclerosis and rheumatoid arthritis.

A common component of chronic inflammatory conditions is polymorphonuclear leukocyte and monocyte infiltration into the site of damage through increased expression of cytokines and adhesion molecules responsible for their recruitment. Overproduction of the cytokine interleukin (IL-6) has been associated with states of chronic inflammation (Bauer M. A. and Herrmann F., *Ann. Hematol.*, 1991, 62, 203). Synthesis of the IL-6 gene is induced by the transcription factor, nuclear factor κB (NF-κB). Interference at this step in the inflammatory process can effectively regulate the uncontrolled proliferative process that occurs in these chronic conditions.

In endothelial cells, 17β-estradiol (E2) inhibits IL-1β induced NF-κB reporter activity and IL-6 expression in an ER dependent fashion (Kurebayashi S. et. al., *J. Steroid Biochem. Molec. Biol.*, 1997, 60, 11). This activity correlates with anti-inflammatory action of E2 in vivo as confirmed in different animal models of inflammation. In models of atherosclerosis, E2 was shown to protect endothelial cell integrity and function and to reduce leukocyte adhesion and intimal accumulation (Adams, M. R. et al., *Arterio.*, 1990, 1051; Sullivan, T. R. et al. *J. Clin. Invst.*, 1995, 96, 2482; Nathan, L. et. al., *Circ. Res.*, 1999, 85, 377). Similar effects of estrogen on the vascular wall also have been demonstrated in animal models of myocardial infarction (Delyani, J. A. et al., *J. Molec. Cell. Cardiol.*, 1996, 28, 1001) and congestive heart failure. Clinically, estrogen replacement therapy (ERT) has been demonstrated to reduce the risk of mortality in patients with both CHF (Reis et. al., *J. Am. Coll. Cardio.*, 2000, 36, 529) and MI (Grodstein, F. et. al., *Ann. Int. Med.*, 2000, 133, 933; Alexander et. al., *J. Am. Coll. Cardio.*, 2001, 38, 1; Grodstein F. et. al., *Ann. Int. Med*, 2001, 135,1). In ERT, clinical studies demonstrated an influence of E2 on the decrease in the production of β-amyloid 1-42 (Aβ42), a peptide central for the formation of senile plaques in Alzheimer's disease (Schonknecht, P. et. al., *Neurosci. Lett.*, 2001, 307, 122).

3-(1-Naphthyl)-3-phenyl-2-cyanopropanoic acid amides have been shown to activate certain ER pathways and have anti-inflammatory activity as described in, for example, U.S. patent application Ser. No. 10/833,678, filed Apr. 28, 2004, incorporated herein by reference in its entirety. These compounds are useful in treating numerous diseases and disorders characterized as having, for example, an inflammatory component. Thus, new and improved methods for the preparation of these compounds are needed. The processes and intermediates provided herein can help meet these and other needs.

SUMMARY OF THE INVENTION

The present invention provides a process for preparing a compound of Formula I:

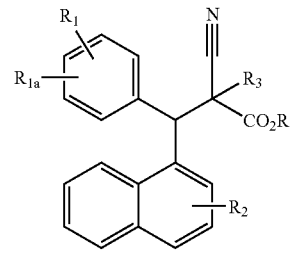

I wherein:

R is $C_{1-6}$ alkyl or benzyl;

$R_1$, $R_{1a}$, and $R_2$ are each, independently, hydrogen, halogen, $C_{1-6}$ alkyl, $C_{1-6}$ alkoxy, $C_{1-6}$ thioalkoxy, nitro, cyano, aryl, $CF_3$, $OCF_3$, $NR_4R_5$ or OH;

$R_3$ is $C_{1-6}$ alkyl, arylalkyl having 1-6 carbons in the alkyl moiety, $C_{2-7}$ alkenyl, cycloalkylmethyl of 3-8 carbons in the cycloalkyl moiety, or Het-alkyl having 1-6 carbons in the alkyl moiety;

$R_4$ and $R_5$ are each independently, hydrogen, $C_{1-6}$ alkyl, aryl, arylalkyl having 1-6 carbon atoms in the alkyl moiety, Het-alkyl having 1-6 carbon atoms in the alkyl moiety, hydroxyalkyl of 1-6 carbons, dihydroxyalkyl of 1-6 carbons, or cycloalkyl of 3-7 carbons;

or $R_4$ and $R_5$ together with the N atom to which they are attached form a 5- or 6-membered heterocycle; and Het is a heterocyclic ring system of 4-14 ring atoms comprising one to four ring-forming heteroatoms;

wherein at least one of $R_1$, $R_{1a}$ and $R_2$ is other than hydrogen; comprising:

a) reacting a compound of Formula II:

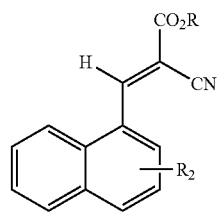

II in a non-protic solvent with a compound of Formula III:

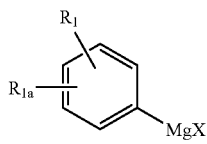

wherein X is Cl, Br or I; and b) reacting a compound of Formula IV:

wherein X' is chloro, bromo, iodo, $OSO_2CH_3$, $OSO_2CF_3$, $OSO_2Ph(4\text{-}Me)$, $OSO_2Ph(4\text{-}CF_3)$, $OSO_2Ph(4\text{-}Br)$, $OSO_2Ph(4\text{-}Cl)$, $OSO_2Ph(4\text{-}F)$, $OSO_2OR_3$, or $OPO_2OR_3$, with the reaction mixture of step a) to form said compound of Formula I.

The present invention further provides embodiments where R is $C_{1\text{-}4}$ alkyl; $R_1$, $R_{1a}$, and $R_2$ are each, independently, hydrogen, $C_{1\text{-}4}$ alkyl, or $C_{1\text{-}4}$ alkoxy; and $R_3$ is $C_{1\text{-}4}$ alkyl.

The present invention further provides embodiments where R is methyl or ethyl; $R_1$ and $R_{1a}$ are each, independently, hydrogen or $C_{1\text{-}4}$ alkoxy; $R_2$ is hydrogen; and $R_3$ is $C_{1\text{-}4}$ alkyl.

The present invention further provides embodiments where $R_1$ is 2'-$OCH_3$; $R_{1a}$ is hydrogen; $R_2$ is hydrogen; and $R_3$ is methyl.

The present invention further provides embodiments where R is methyl; $R_1$ is 2'-$OCH_3$; $R_{1a}$ is hydrogen; $R_2$ is hydrogen; and $R_3$ is methyl.

The present invention further provides embodiments where X' is $OSO_2CH_3$, $OSO_2OR_3$, Br, or I, and in yet further embodiments, X' is I. In some embodiments, $R_3$—X' is methyl iodide.

The present invention further provides embodiments where X' is $OSO_2OR_3$, and in yet further embodiments, $R_3$—X' is dimethyl sulfate.

The present invention further provides embodiments where the reacting of step a) is carried out in an ether solvent such as tetrahydrofuran.

The present invention further provides embodiments where the compound of Formula I is isolated such as by precipitating the compound of Formula I from the reaction mixture of step b) and separating the precipitated compound of Formula I from the reaction mixture by filtration.

The present invention further provides embodiments where isolation can be carried out by:

c) removing at least a portion of the non-protic solvent from the reaction mixture of step b) to form a reduced volume reaction mixture;

d) adding protic solvent to the reduced volume reaction mixture;

e) optionally adding acid to said reduced volume reaction mixture of step d) until the pH is from about 3 to about 7 to form a pH-adjusted reaction mixture; and f) filtering said pH-adjusted reaction mixture to isolate said compound of Formula I.

The present invention further provides embodiments where the compound of Formula I has the Formula Ia:

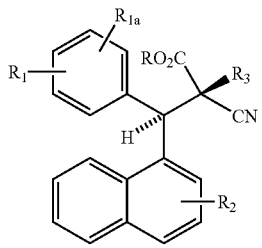

DETAILED DESCRIPTION OF THE INVENTION

The present invention is directed to, inter alia, processes for the preparation of compounds of Formula I that are useful, not only as therapeutics, but also as intermediates in the preparation of 3-(1-naphthyl)-3-phenyl-2-cyanopropanoic acid amides (see, e.g., U.S. patent application Ser. No. 10/833,678, filed Apr. 28, 2004, incorporated herein by reference in its entirety), which are useful in the treatment of inflammatory disorders. According to some embodiments, the present invention provides methods of preparing 3-(1-naphthyl)-3-phenyl-2-cyanopropanoic acid alkyl and benzyl esters without the need for isolation of reaction intermediates. According to further embodiments, the present invention provides processes for the isolation of compounds of Formula I while foregoing the use of organic extraction via providing methods to directly precipitate out the desired product in substantial yield and purity.

A general outline of the processes of the present invention is provided in Scheme I, where constituent members of the depicted compounds of Formulas I, II, III, and IV are defined hereinbelow.

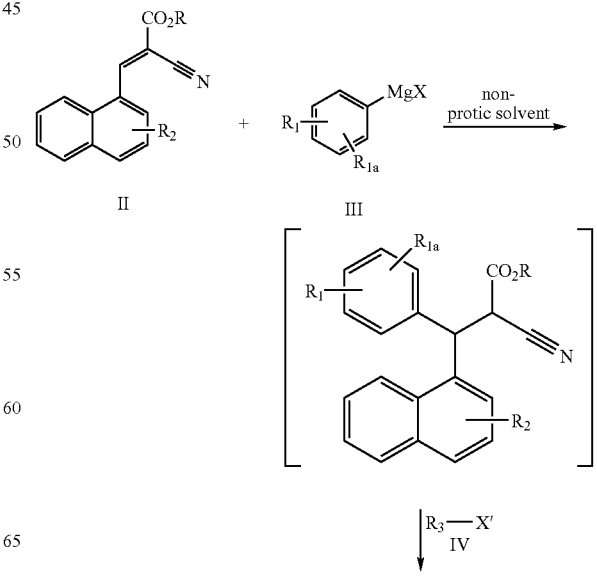

Scheme I

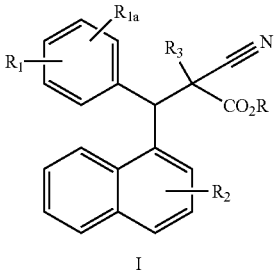

In some embodiments, the present invention provides a process for preparing a compound of Formula I:

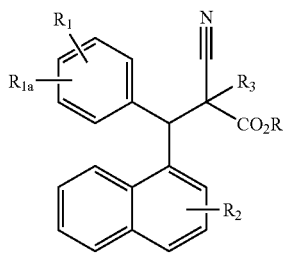

wherein:

R is $C_{1-6}$ alkyl or benzyl;

$R_1$, $R_{1a}$, and $R_2$ are each, independently, hydrogen, halogen, $C_{1-6}$ alkyl, $C_{1-6}$ alkoxy, $C_{1-6}$ thioalkoxy, nitro, cyano, aryl, $CF_3$, $OCF_3$, $NR_4R_5$ or OH;

$R_3$ is $C_{1-6}$ alkyl, arylalkyl having 1-6 carbons in the alkyl moiety, $C_{2-7}$ alkenyl, cycloalkylmethyl of 3-8 carbons in the cycloalkyl moiety, or Het-alkyl having 1-6 carbons in the alkyl moiety;

$R_4$ and $R_5$ are each independently, hydrogen, $C_{1-6}$ alkyl, aryl, arylalkyl having 1-6 carbon atoms in the alkyl moiety, Het-alkyl having 1-6 carbon atoms in the alkyl moiety, hydroxyalkyl of 1-6 carbons, dihydroxyalkyl of 1-6 carbons, or cycloalkyl of 3-7 carbons;

or $R_4$ and $R_5$ together with the N atom to which they are attached form a 5- or 6-membered heterocycle; and Het is a heterocyclic ring system of 4-14 ring atoms comprising one to four ring-forming heteroatoms;

wherein at least one of $R_1$, $R_{1a}$ and $R_2$ is other than hydrogen; comprising:

a) reacting a compound of Formula II:

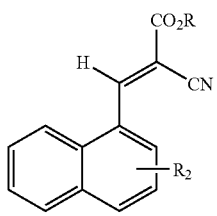

in a non-protic solvent with a compound of Formula III:

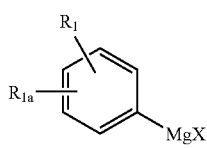

wherein X is Cl, Br or I; and b) reacting a compound of Formula IV:

$$R_3 - X'$$  IV wherein X' is chloro, bromo, iodo, $OSO_2CH_3$, $OSO_2CF_3$, $OSO_2Ph(4\text{-Me})$, $OSO_2Ph(4\text{-}CF_3)$, $OSO_2Ph(4\text{-Br})$, $OSO_2Ph(4\text{-Cl})$, $OSO_2Ph(4\text{-F})$, $OSO_2OR_3$, or $OPO_2OR_3$, with the reaction mixture of step a) to form said compound of Formula I.

In some embodiments of the invention R is $C_{1-4}$ alkyl; $R_1$, $R_{1a}$, and $R_2$ are each, independently, hydrogen, $C_{1-4}$ alkyl, or $C_{1-4}$ alkoxy; and $R_3$ is $C_{1-4}$ alkyl.

In further embodiments of the invention R is methyl or ethyl; $R_1$ and $R_{1a}$ are each, independently, hydrogen or $C_{1-4}$ alkoxy; $R_2$ is hydrogen; and $R_3$ is $C_{1-4}$ alkyl.

In further embodiments of the invention $R_1$ is 2'-$OCH_3$; $R_{1a}$ is hydrogen; $R_2$ is hydrogen; and $R_3$ is methyl.

In further embodiments of the invention R is methyl; $R_1$ is 2'-$OCH_3$; $R_{1a}$ is hydrogen; $R_2$ is hydrogen; and $R_3$ is methyl.

In further embodiments, X' is $OSO_2CH_3$, $OSO_2OR_3$, Br, or I, and in yet further embodiments, X' is I. In some embodiments, $R_3$—X' is methyl iodide.

In further embodiments, X' is $OSO_2OR_3$, and in yet further embodiments, $R_3$—X' is dimethyl sulfate.

In some embodiments, the reacting of step a) is carried out in an ether solvent such as tetrahydrofuran.

In further embodiments, the compound of Formula I is isolated such as by precipitating the compound of Formula I from the reaction mixture of step b) and separating the precipitated compound of Formula I from the reaction mixture by filtration. In some embodiments, isolation can be carried out by:

c) removing at least a portion of the non-protic solvent from the reaction mixture of step b) to form a reduced volume reaction mixture;

d) adding protic solvent to the reduced volume reaction mixture;

e) optionally adding acid to said reduced volume reaction mixture of step d) until the pH is from about 3 to about 7 to form a pH-adjusted reaction mixture; and f) filtering said pH-adjusted reaction mixture to isolate said compound of Formula I.

The reacting of step a) can be carried out at any suitable temperature or pressure. For example, the reaction temperature can range from about −20° C. to reflux temperature of the non-protic solvent. In some embodiments, the compound of Formula III is added to a solution of Formula II at reduced temperature (e.g., below room temperature). The reduced temperature can be from about −20 to about 10, about −10 to about 10, about 0 to about 10, or about 5° C. Suitable amounts of compounds of Formula II and III for carrying out the reacting of step a) can be readily determined by the skilled artisan. Generally, a molar ratio of a compound of Formula II to a compound of Formula III of about 1:1 is suitable. Reaction duration is sufficient time for the reacting of step a) to go substantially to completion as can be monitored by any suitable method known in the art. In some embodiments, the reacting of step a) is carried out for about 15 minutes to about 3 hours, about 30 minutes to about 2 hours, or about 1 to about 2 hours. The reacting of step a) also can be conducted under inert atmosphere.

The reacting of step b) can be carried out without the isolation of any of the products of the reacting of step a). For example, the compound of Formula IV can be added directly to the reaction mixture of step a), such as after the reaction of step a) has gone substantially to completion. The amount of compound of Formula IV is typically enough to provide maximum yield. Example amounts include from about 1 eq to about 10 eq, 2 eq to about 5 eq, 3 eq to about 6 eq, or about 4 eq relative to the amount of compound of Formula II. The combining can be carried out at any suitable temperature such as an elevated temperature (e.g., above room temperature). In some embodiments, the elevated temperature ranges from about 30 to about 120, 30 to about 80, or about 30 to about 50° C. In some embodiments, the elevated temperature is about 40° C. Reaction duration for the combining step typically allows the reaction to go substantially to completion. About 1 to about 48 hours, about 12 to about 36 hours, about 24 to about 30 hours, or about 28 hours is suitable.

Isolation of the compound of Formula I can be carried out by precipitating the compound of Formula I from the reaction mixture of step b). Precipitation can be induced by reducing the volume of solvent in the mixture, such as by distillation. Precipitation also can be induced by addition of protic solvent such as water or alcohol (e.g., methanol) and/or the addition of acid such as HCl (e.g., 0.5 N HCl). Cooling of the reaction mixture, or a combination of any of the above precipitating techniques also can induce precipitation suitable for isolation of the compound of Formula I. Once a precipitate has formed, it can be collected by filtration according to techniques well known in the art.

In some embodiments, the processes of the present invention result in preparation of the compound of Formula I enriched (e.g., de>about 50%, about 75%, about 85%, about 90%, about 95%, or about 98%) in one diastereoisomer. For example, the compound of Formula I can have the Formula Ia.

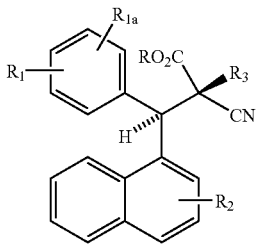

Ia

There are numerous advantages to the processes described herein that are readily apparent to the skilled artisan. For example, the "one pot" approach described herein, which avoids the isolation and/or purification of intermediates, is a desirable feature of any synthetic process and results in a more efficient, less costly preparative route. Additionally, isolation of product without the use of solvent extraction techniques greatly reduces preparation time as well as the amount of solvent waste.

The term "alkyl", employed alone or in combination with other terms, is defined herein as, unless otherwise stated, either a straight-chain or branched saturated hydrocarbon moiety. In some embodiments, the alkyl moiety contains 1 to 12, 1 to 10, 1 to 8, 1 to 6, or 1 to 4 carbon atoms. Examples of saturated hydrocarbon alkyl moieties include, but are not limited to, chemical groups such as methyl, ethyl, n-propyl, isopropyl, n-butyl, tert-butyl, isobutyl, sec-butyl; higher homologs such as n-pentyl, n-hexyl, n-heptyl, n-octyl, and the like.

The term "cycloalkyl", employed alone or in combination with other terms, is defined herein as, unless otherwise stated, a monocyclic, bicyclic, tricyclic, fused, bridged, or spiro monovalent saturated hydrocarbon moiety of 3-10 carbon atoms, e.g., 3-8 carbon atoms. Any suitable ring position of the cycloalkyl moiety can be linked covalently to the defined chemical structure. Examples of cycloalkyl moieties include, but are not limited to, chemical groups such as cyclopropyl, cyclobutyl, cyclopentyl, cyclohexyl, cycloheptyl, norbornyl, adamantyl, spiro[4.5]decanyl, and homologs, isomers, and the like.

The terms "halo" or "halogen", employed alone or in combination with other terms, is defined herein as, unless otherwise stated, fluoro, chloro, bromo, or iodo.

The term "aryl", employed alone or in combination with other terms, is defined herein as, unless otherwise stated, an aromatic carbocyclic moiety of up to 14 carbon atoms (e.g., 6-14 carbon atoms), which can be a single ring (monocyclic) or multiple rings (bicyclic, up to three rings) fused together or linked covalently. Any suitable ring position of the aryl moiety can be linked covalently to the defined chemical structure. Examples of aryl moieties include, but are not limited to, chemical groups such as phenyl, 1-naphthyl, 2-naphthyl, dihydronaphthyl, tetrahydronaphthyl, biphenyl, anthryl, phenanthryl, fluorenyl, indanyl, biphenylenyl, acenaphthenyl, acenaphthylenyl, and the like.

The term "arylalkyl", employed alone or in combination with other terms, is defined herein as, unless otherwise stated, an aryl, as herein before defined, suitably substituted on any open ring position with an alkyl moiety wherein the alkyl chain is a saturated hydrocarbon moiety. In some embodiments, the alkyl moiety has from 1 to 8, 1 to 6, or 1 to 4 carbon atoms. Examples of arylalkyl moieties include, but are not limited to, chemical groups such as benzyl, 1-phenylethyl, 2-phenylethyl, diphenylmethyl, 3-phenylpropyl, 2-phenylpropyl, fluorenylmethyl, and homologs, isomers, and the like.

The term "Het", employed alone or in combination with other terms, is defined herein as, unless otherwise stated, a heterocyclic ring system having 4-14 ring atoms, which can be a single ring (monocyclic) or multiple rings (bicyclic, up to three rings) fused together or linked covalently. The rings contain from one to four hetero atoms selected from nitrogen (N), oxygen (O), and sulfur (S), wherein the nitrogen or sulfur atom(s) are optionally oxidized, or the nitrogen atom(s) are optionally quaternized. Any suitable ring position of the heterocyclic moiety can be covalently linked to the defined chemical structure. Het can be saturated or unsaturated. Het also can be aromatic or non-aromatic. Examples Het moieties include, but are not limited to, furan, thiophene, pyrrole, N-methylpyrrole, pyrazole, N-methylpyrazole, imidazole, N-methylimidazole, oxazole, isoxazole, thiazole, isothiazole, 1H-tetrazole, 1-methyltetrazole, 1,3,4-oxadiazole, 1H-1,2,4-triazole, 1-methyl-1,2,4-triazole 1,3,4-triazole, 1-methyl-1,3,4-triazole, pyridine, pyrimidine, pyrazine, pyridazine, benzoxazole, benzisoxazole, benzothiazole, benzofuran, benzothiophene, thianthrene, dibenzo[b,d]furan, dibenzo[b,d]thiophene, benzimidazole, N-methylbenzimidazole, indole, indazole, quinoline, isoquinoline, quinazoline, quinoxaline, purine, pteridine, 9H-carbazole, β-carboline, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothienyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydro-1,4-dioxanyl, tetrahydrofuranyl, tetrahydrothienyl, tetrahydroquinolinyl, tetrahydroisoquinolinyl, and the like.

The term "Het-alkyl", employed alone or in combination with other terms, is defined herein as, unless otherwise stated, an alkyl substituted by at least one Het. Examples of Het-alkyl moieties include, but are not limited to, chemical groups such as furanylmethyl, thienylethyl, indolylmethyl, and the like.

The term "hydroxyalkyl", employed alone or in combination with other terms, is defined herein as, unless otherwise stated, a ($C_1$-$C_6$) straight chain hydrocarbon, terminally substituted with a hydroxyl group. Examples of hydroxyalkyl moieties include chemical groups such as —$CH_2OH$, —$CH_2CH_2OH$, —$CH_2CH_2CH_2OH$, and higher homologs. Similarly, dihydroxyalkyl indicates an alkyl moiety that is substituted by two hydroxyl groups.

The term "alkoxy", employed alone or in combination with other terms, is defined herein as, unless otherwise stated, —O-alkyl. Examples of alkoxy moieties include, but are not limited to, chemical groups such as methoxy, ethoxy, isopropoxy, sec-butoxy, tert-butoxy, and homologs, isomers, and the like.

The term "alkylthio" or "thioalkoxy" employed alone or in combination with other terms, is defined herein as, unless otherwise stated, —S-alkyl. Examples of alkylthio moieties include, but are not limited to, chemical groups such as methylthio, ethylthio, isopropylthio, sec-butylthio, tert-butylthio, and homologs, isomers, and the like.

As used herein, the term "precipitating" is used as known in the art and generally refers to the formation of a solid (e.g., precipitate) from a solution in which the solid is dissolved. The solid can be amorphous or crystalline. Methods of precipitation are well known in the art and include, for example, increasing the proportion of solvent in which a solute is insoluble, decreasing temperature, chemically transforming the solute such that it becomes no longer soluble in its solvent, and the like.

As used herein, the term "reacting" refers to the bringing together of designated chemical reactants such that a chemical transformation takes place generating a compound different from any initially introduced into the system. Reacting can take place in the presence or absence of solvent.

As used herein, the term "combining" refers to the bringing together of designated chemical reactants with any other chemical substance or mixture, typically resulting in the production of additional chemical compounds or substances.

The processes described herein can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), or mass spectrometry, or by chromatography such as high performance liquid chromatograpy (HPLC) or thin layer chromatography.

The reactions of the processes described herein can be carried out in suitable solvents, which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

The term protic solvent refers to a solvent that is capable of functioning as an acid for purposes of protonating any unreacted, strongly basic reaction intermediates. Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol.

The term non-protic solvent refers to an organic solvent that is not readily deprotonated in the presence of a strongly basic reactant. Suitable non-protic solvents can include, by way of example and without limitation, ethers, dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable ether solvents include: diethoxymethane, tetrahydrofuran, 1,3-dioxane, 1,4-dioxane, furan, diethyl ether, diiospropyl ether, dibutyl ether, ethylene glycol dimethyl ether, ethylene glycol diethyl ether, diethylene glycol dimethyl ether, diethylene glycol diethyl ether, triethylene glycol dimethyl ether, anisole, or t-butyl methyl ether.

The reactions of the processes described herein can be carried out at appropriate temperatures, which can be readily determined by the skilled artisan. Reaction temperatures will depend on, for example, the melting and boiling points of the reagents and solvent, if present; the thermodynamics of the reaction (e.g., vigorously exothermic reactions are typically carried out at reduced temperatures); and the kinetics of the reaction (e.g., a high activation energy barrier typically necessitates elevated temperatures). "Elevated temperatures" refers to temperatures above room temperature (about 20° C.) and "reduced temperatures" refers to temperatures below room temperature.

The reactions of the processes described herein can be carried out in air or under an inert atmosphere. Typically, reactions containing reagents or products that are substantially reactive with air can be carried out using air-sensitive synthetic techniques that are well known to the skilled artisan.

The compounds of the present invention can contain an asymmetric atom, and some of the compounds can contain one or more asymmetric atoms or centers, which thus, can give rise to optical isomers (enantiomers) and diastereomers. While shown without respect to the stereochemistry in Formula I, the present invention includes such optical isomers (enantiomers) and diastereomers (geometric isomers); as well as the racemic and resolved, enantiomerically pure R and S stereoisomers; as well as other mixtures of the R and S stereoisomers and pharmaceutically acceptable salts thereof. Optical isomers can be obtained in pure form by standard procedures known to those skilled in the art, and include, but are not limited to, diastereomeric salt formation, kinetic resolution, and asymmetric synthesis. It is also understood that this invention encompasses all possible regioisomers, and mixtures thereof, which can be obtained in pure form by standard separation procedures known to those skilled in the art, and include, but are not limited to, column chromatography, thin-layer chromatography, and high-performance liquid chromatography.

It is appreciated that certain features of the invention, which are, for clarity, described in the context of separate embodiments, also can be provided in combination in a single embodiment. Conversely, various features of the invention which are, for brevity, described in the context of a single embodiment, also can be provided separately or in any suitable subcombination.

The invention will be described in greater detail by way of specific examples. The following examples are offered for illustrative purposes, and are not intended to limit the invention in any manner. Those of skill in the art will readily recognize a variety of noncritical parameters that can be changed or modified to yield essentially the same results.

EXAMPLE 1

Preparation of 2-Cyano-3-(2-Methoxy-Phenyl)-2-Methyl-3-Naphthalen -1-Yl-Propionic Acid Methyl Ester (3)

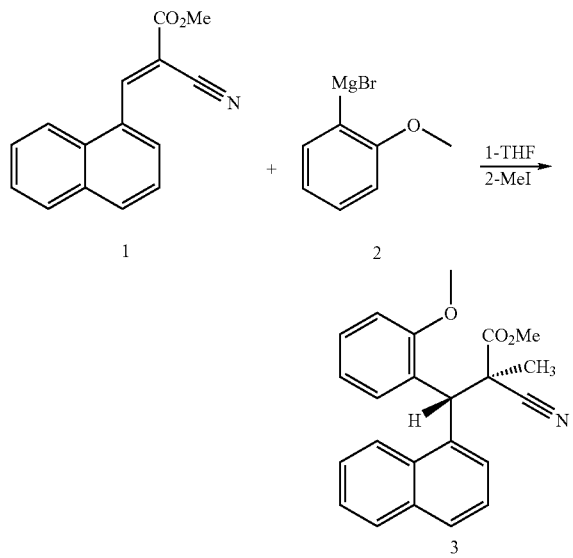

To a 5-liter, 4-neck flask equipped with a mechanical stirrer, a condenser fitted with nitrogen inlet, a cooling bath and thermal couple were added 882 g anhydrous THF and 250 g (1.05 mol) 2-cyano-3-naphthalen-1-yl-acrylic acid methyl ester 1. The mixture was cooled to 5° C. and 1098 g (1.09 mol) of a 1 M THF solution of 2-methoxyphenylmagnesium bromide 2 was slowly charged into the reaction mixture through an addition funnel while maintaining the temperature at 0-10° C. The mixture was stirred for an additional 30 min. Methyl iodide (598 g, 4.21 mol) then was added in one portion. The mixture was stirred at 40° C. for 28 hours and then cooled to 25° C. The mixture was treated with 943 g of 0.5 N HCl and the lower aqueous phase was separated and retained. The organic layer was concentrated by distillation until 871 g distillate was collected. The organic concentrate then was cooled to 35° C. and the aqueous layer was combined with the organic. To the mixture then was added 506 g methanol. The mixture was cooled to 0° C. and the product was filtered. The wet cake was washed with a mixture of 333 g of methanol and 666 g of water. The product 3 was dried in an oven at 55° C. under vacuum. Yield: 306 g, 81%. The diastereomeric excess was typically 100%.

Various modifications of the invention, in addition to those described herein, will be apparent to those skilled in the art from the foregoing description. Such modifications also are intended to fall within the scope of the appended claims. Each reference cited in the present application, including but not limited to printed publications, patents and patent applications, is incorporated herein by reference in its entirety.

What is claimed is:

1. A process for preparing a compound of Formula I:

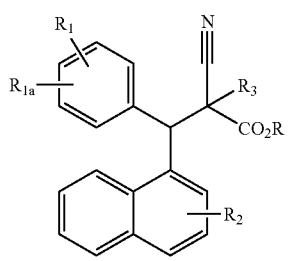

wherein:

R is $C_{1-6}$ alkyl or benzyl;

$R_1$, $R_{1a}$, and $R_2$ are each, independently, hydrogen, halogen, $C_{1-6}$ alkyl, $C_{1-6}$ alkoxy, $C_{1-6}$ thioalkoxy, nitro, cyano, aryl, $CF_3$, $OCF_3$, $NR_4R_5$ or OH;

$R_3$ is $C_{1-6}$ alkyl, arylalkyl having 1-6 carbons in the alkyl moiety, $C_{2-7}$ alkenyl, cycloalkylmethyl of 3-8 carbons in the cycloalkyl moiety, or Het-alkyl having 1-6 carbons in the alkyl moiety;

$R_4$ and $R_5$ are each independently, hydrogen, $C_{1-6}$ alkyl, aryl, arylalkyl having 1-6 carbon atoms in the alkyl moiety, Het-alkyl having 1-6 carbon atoms in the alkyl moiety, hydroxyalkyl of 1-6 carbons, dihydroxyalkyl of 1-6 carbons, or cycloalkyl of 3-7 carbons;

or $R_4$ and $R_5$ together with the N atom to which they are attached form a 5- or 6-membered heterocycle; and Het is a heterocyclic ring system of 4-14 ring atoms comprising one to four ring-forming heteroatoms;

wherein at least one of $R_1$, $R_{1a}$ and $R_2$ is other than hydrogen;

comprising:

a) reacting a compound of Formula II:

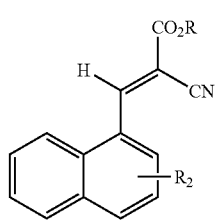

in a non-protic solvent with a compound of Formula III:

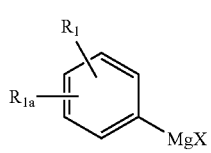

wherein $R_1$, $R_{1a}$, $R_2$ are defined above and X is Cl, Br or I; and b) reacting a compound of Formula IV:

$$R_3—X' \qquad \text{IV}$$

wherein $R_3$ is as defined above and X' is chloro, bromo, iodo, $OSO_2CH_3$, $OSO_2CF_3$, $OSO_2Ph(4\text{-}Me)$, $OSO_2Ph(4\text{-}CF_3)$, $OSO_2Ph(4\text{-}Br)$, $OSO_2Ph(4\text{-}Cl)$, $OSO_2Ph(4\text{-}F)$, $OSO_2OR_3$, or $OPO_2OR_3$,
with the reaction mixture of step a) to form said compound of Formula I.

2. The process of claim 1 wherein R is $C_{1-4}$ alkyl.

3. The process of claim 2, wherein R is methyl or ethyl.

4. The process of claim 2, wherein R is methyl

5. The process of claim 1, wherein $R_1$, $R_{1a}$, and $R_2$ are each, independently, hydrogen, $C_{1-4}$ alkyl, or $C_{1-4}$ alkoxy.

6. The process of claim 5, wherein $R_1$ and $R_{1a}$, are each, independently, hydrogen, $C_{1-4}$ alkyl, or $C_{1-4}$ alkoxy, and $R_2$ is hydrogen.

7. The process of claim 1, wherein $R_3$ is $C_{1-4}$ alkyl.

8. The process of claim 7, wherein $R_3$ is methyl.

9. The process of claim 1, wherein R is methyl or ethyl, $R_1$, $R_{1a}$, and $R_2$ are each, independently, hydrogen, $C_{1-4}$ alkyl, or $C_{1-4}$ alkoxy, and $R_3$ is $C_{1-4}$ alkyl.

10. The process of claim 1, wherein $R_1$ is 2'-$OCH_3$, $R_{1a}$ is hydrogen, $R_2$ is hydrogen, and $R_3$ is methyl.

11. The process of claim 1, wherein R is methyl, $R_1$ is 2'-$OCH_3$, $R_{1a}$ is hydrogen, $R_2$ is hydrogen, and $R_3$ is methyl.

12. The process of claim 1, wherein X' is $OSO_2CH_3$, $OSO_2OR_3$, Br, or I.

13. The process of claim 1, wherein X' is I.

14. The process of claim 1, wherein $R_3$—X' is methyl iodide.

15. The process of claim 1, wherein X' is $OSO_2OR_3$.

16. The process of claim 1, wherein $R_3$—X' is dimethyl sulfate.

17. The process of claim 1, wherein said non-protic solvent is an ether.

18. The process of claim 17, wherein said ether is tetrahydrofuran.

19. The process of claim 1, wherein said compound of Formula I is isolated.

20. The process of claim 19, wherein said compound of Formula I is isolated by precipitating said compound of Formula I from the reaction mixture of step b) and separating said precipitated compound of Formula I by filtration.

21. The process of claim 19, wherein said compound of Formula I is isolated by the process comprising:

c) removing at least a portion of said non-protic solvent from the reaction mixture of step b) to form a reduced volume reaction mixture;

d) adding a protic solvent to said reduced volume reaction mixture;

e) optionally adding an acid to said reduced volume reaction mixture until the pH is from about 3 to about 7 to form a pH-adjusted reaction mixture; and f) filtering said pH-adjusted reaction mixture to isolate said compound of Formula I.

22. The process of claim 1, wherein said compound of Formula I has the Formula Ia:

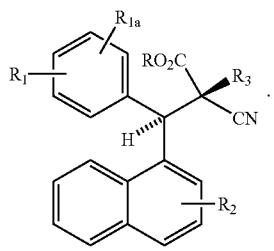

* * * * *